United States Patent [19]

Rickwood

[11] Patent Number: 4,851,530
[45] Date of Patent: Jul. 25, 1989

[54] SPIRO-OXAZINE COMPOUNDS

[75] Inventor: Martin Rickwood, Southport, England

[73] Assignee: Pilkington plc, St. Helens, England

[21] Appl. No.: 122,463

[22] Filed: Nov. 19, 1987

[30] Foreign Application Priority Data

Nov. 21, 1986 [GB] United Kingdom ............... 8627859

[51] Int. Cl.$^4$ ................ C07D 498/20; C07D 498/22
[52] U.S. Cl. ...................................................... 544/71
[58] Field of Search .......................................... 544/71

[56] References Cited

U.S. PATENT DOCUMENTS

| | | | |
|---|---|---|---|
| 3,508,810 | 7/1967 | Baltzer | 350/160 |
| 3,578,602 | 5/1971 | Ono et al. | 252/300 |
| 4,215,010 | 7/1980 | Hovey et al. | 252/300 |
| 4,634,767 | 1/1987 | Hoelscher et al. | 544/71 |
| 4,637,698 | 1/1987 | Kwak et al. | 351/163 |
| 4,719,296 | 1/1988 | Irie et al. | 544/71 |

FOREIGN PATENT DOCUMENTS

| | | |
|---|---|---|
| 0141407 | 5/1985 | European Pat. Off. . |
| 3602087 | 7/1986 | Fed. Rep. of Germany . |
| 62-155283 | 7/1987 | Japan . |
| WO85/02619 | 6/1985 | PCT Int'l Appl. . |
| WO87/00524 | 1/1987 | PCT Int'l Appl. . |
| 2117390 | 10/1983 | United Kingdom . |
| 2184734 | 1/1987 | United Kingdom . |

*Primary Examiner*—Richard L. Raymond
*Attorney, Agent, or Firm*—Burns, Doane, Swecker & Mathis

[57] ABSTRACT

An azaindoline spiro-oxazine of the general formula (I):

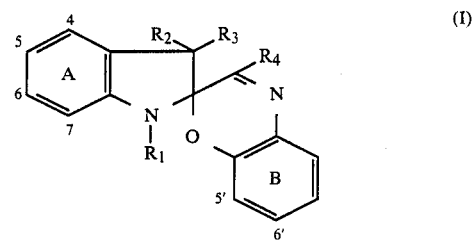

wherein $R_1$ represents an aliphatic or aromatic group;

each of $R_2$ and $R_3$ independently represents a hydrogen atom, an aliphatic or aromatic group or an alkoxy group, or $R_2$ and $R_3$ together with the carbon atom to which they are attached represent an alicyclic group;

$R_4$ represents a hydrogen atom or an aliphatic or aromatic group;

ring A contains one or more nitrogen atoms in the ring and may be unsubstituted or substituted provided that there is no substituent on any nitrogen atom in the ring; and ring B may be unsubstituted or substituted by at least one substituent provided that the 6'-position in ring B is not substituted by an amine function or hydroxyl group. The spiro-oxazine compounds are useful for imparting photochromic properties to a plastics host material such as a plastics lens.

13 Claims, No Drawings

SPIRO-OXAZINE COMPOUNDS

FIELD OF THE INVENTION

The present invention relates to spiro-oxazine compounds.

DESCRIPTION OF THE PRIOR ART

Spiro-oxazine compounds have been found to be useful for imparting photochromic properties to a polymerised host material such as a plastic lens. Examples of typical spiro-oxazine compounds and of their use can be found in U.S. Pat. No. 4,215,010, European Patent Application No. 0141407, U.K. Patent Application Nos. 2171404 and 2117390, International Patent Application No. 85/02619 and U.K. Patent Application No. 8610709.

We have now found that certain new azaindoline spiro-oxazines are also useful for imparting photochromism to a polymerised host material such as a plastic lens.

An advantage of the azaindoline spiro-oxazine compounds of the invention is that when they are incorporated in a plastics host material the colour imparted to the host material when the spiro-oxazine is in the faded or unactivated state is relatively pale when compared to known photochromic spiro-oxazine compounds. Furthermore, the colour imparted to the plastics host material by the present spiro-oxazine compounds when they are in their darkened or activated state is also much less intense than that obtained with known photochromic spiro-oxazine compounds. As a result, the azaindoline spiro-oxazine compounds of the invention are particularly useful for producing photochromic plastic products such as ophthalmic lenses having a "white" base condition and an attractive cosmetic photochromism.

BRIEF SUMMARY OF THE INVENTION

Accordingly, the present invention provides azaindoline spiro-oxazines of the general formula (I):

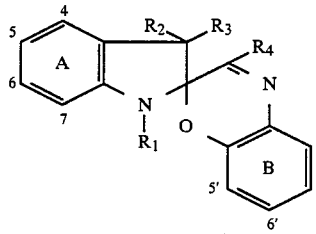

wherein $R_1$ represents an aliphatic or aromatic group;

each of $R_2$ and $R_3$ independently represents a hydrogen atom, an aliphatic or aromatic group or an alkoxy group, or $R_2$ and $R_3$ together with the carbon atom to which they are attached represent an alicyclic group;

$R_4$ represents a hydrogen atom or an aliphatic or aromatic group;

ring A contains one or more nitrogen atoms in the ring and may be unsubstituted or substituted, provided that there is no substituent on any nitrogen atom in the ring; and ring B may be unsubstituted or substituted by at least one substituent provided that the 6'-position in ring B is not substituted by an amine function or hydroxyl group.

DETAILED DESCRIPTION OF THE INVENTION

Preferably, $R_1$ represents an alkyl, alkenyl, phenylalkyl (such as benzyl) or substituted phenyl group.

Preferably, each of $R_2$ and $R_3$ independently represents a hydrogen atom, or an alkyl, alkenyl, phenyl, phenylalkyl (such as benzyl), mono-, di- or tri-substituted phenyl or alkoxy group, or $R_2$ and $R_3$ together with the carbon atom to which they are attached represent an alicyclic ring such as a spirocarbon e.g. hexane, norbornane and adamantane.

Preferably, $R_4$ represents a hydrogen atom, or an alkyl, aryl, or heteroaryl group, most preferably a hydrogen atom.

As defined above, each of rings A and B may carry one or more substituents; these substituents are preferably selected from:

(i) a group of the formula —R, —OR, —SR, —COR, —COOR wherein R represents H, alkyl, aryl or heteroaryl; with the proviso that no hydroxy group may be present at the 6'-position of ring B;

(ii) —X, —CH$_2$X, —CHX$_2$, —CX$_3$ wherein X represents halogen;

(iii) —NO$_2$, —CN, —SCN;

(iv) a ring system fused to ring A or B and comprising aromatic or hetero-aromatic rings or alicyclic or heteroalicyclic rings.

(v) an amine functionality of general formula —NR'R" wherein each of R' and R" independently represents a hydrogen atom, or an alkyl, cycloalkyl or phenyl group or a substituted derivative thereof, or an amine functionality which is a cycloheteroalkyl ring, which ring includes one or more heteroatoms, with the proviso that no amine functionality may be present at the 6'-position of ring B.

Preferred compounds of formula (I) are those represented by formula (II) below:

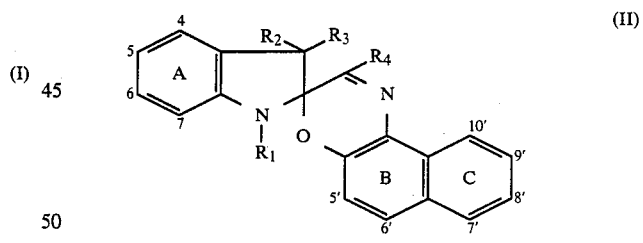

wherein $R_1$, $R_2$, $R_3$ and $R_4$ are as defined above for the compounds of formula (I), ring B may be unsubstituted or substituted at position 5' and/or 6', with the proviso that no hydroxy or amine functionality is present at the 6'-position of ring B; and ring C may contain one or more nitrogen atoms in the ring and may be unsubstituted or substituted at one or more of positions 7', 8', 9' or 10'.

The substituents on ring C, if present, are preferably selected from substituents of types (i), (ii), (iii), (iv) and (v) as defined above.

In a preferred class of compounds in accordance with the invention ring A contains a ring nitrogen atom in the 7-position, or in the 4-position. In another group of preferred compounds ring A contains two ring nitrogen atoms, one in the 4-position and one in the 7-position.

Examples of typical ring A substituents are alkyl or alkoxy groups such as methyl or methoxy groups typically at the 5- or 6-position.

In a further preferred embodiment of the invention, in the compounds of formula (II) ring C contains a nitrogen atom in the 7'-position, and/or optionally carries a substituent, typically a hydroxy or methoxy group, at the 9'-position.

Preferred compounds in accordance with the invention are those having the general formulae

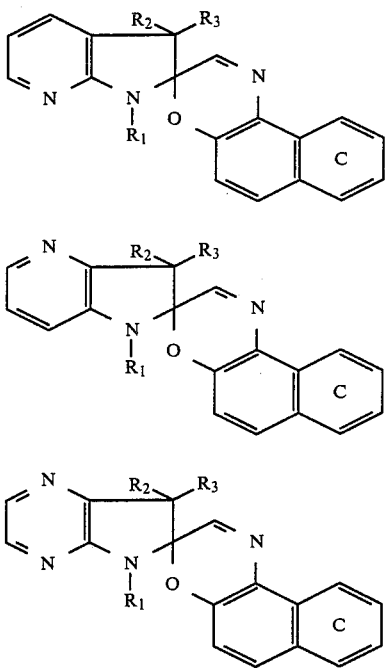

wherein each of $R_1$, $R_2$ and $R_3$ is a $C_{1-4}$ alkyl group, ring A may optionally carry a $C_{1-4}$ alkyl or $C_{1-4}$ alkoxy group in the 6-position, and ring C may optionally have a nitrogen atom in the 7'-position and/or may optionally carry a $C_{1-4}$ alkoxy group in the 9'-position.

The compounds of general formula (I) may be prepared by the general preparative method described in U.S. Pat. No. 3,578,602, which is based on the following reaction scheme

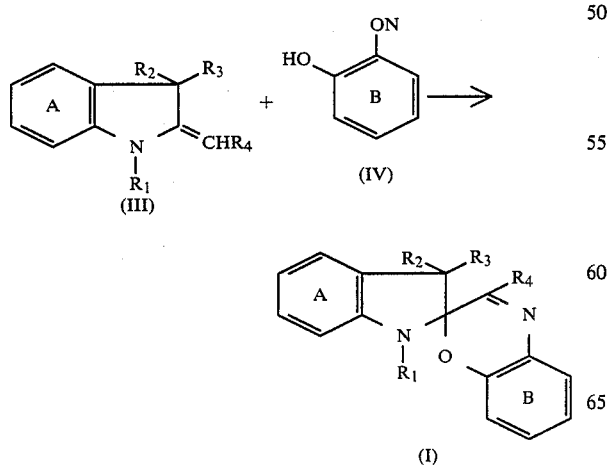

wherein $R_1$, $R_2$, $R_3$ and $R_4$ and rings A and B are as defined above.

In order to prepare the compounds of formula (I), the appropriate nitroso-hydroxy derivative of formula (IV) is reacted with the appropriate indoline of formula (III). Alternatively, an indolenium salt, such as a methiodide, can be used instead of the indoline of formula (III).

The two starting materials are generally reacted together by refluxing in a solvent such as trichloroethylene, benzene or toluene. If an indolenium salt is used, a base such as the triethylamine should be present. The desired spiro-oxazine product is separated and purified by conventional techniques such as chromatographic separation and crystallisation.

It will be clear to a person skilled in the art that other known reaction schemes may be used to produce the novel compounds according to the present invention. In particular such an alternative known reaction scheme is required when a nitrogen group is a substituent on ring C.

The azaindoline spiro-oxazine compounds of the present invention are particularly useful for imparting photochromic properties to a polymerised host material, particularly a plastic ophthalmic lens.

The compounds of the invention when incorporated in a plastic host material give less background colour in their faded condition than do other known spiro-oxazine compounds, and the photochromic effect obtained when the compounds are exposed to actinic radiation is relatively pale when compared to the photochromic effect obtained with known compounds. This provides the possibility of producing plastic products having a "white" base colouration and attractive cosmetic photochromism. The compounds of the present invention are also found to have a good fatigue life and continue to exhibit the desired photochromic effects over a prolonged period.

The present invention is illustrated further by the following Examples.

EXAMPLE 1

A solution of 1,3,3-trimethyl-2-methylene-7-azaindole (3.5 g; 0.02 mol) and 1-nitroso-2-naphthol (3.5 g; 0.02 mol) in benzene (50 ml) was heated under reflux for 24 hours. The benzene was removed and the oil produced was adsorped onto silica and chromatographed in the silica using diethyl ether-n-hexane as the eluent. Upon evaporation of the eluent 1,3,3-trimethylspiro(7-azaindoline-2-3'-3H-naphtho(2,1-b)(1,4)oxazine) of the formula (V) below was obtained. The physical data for this compound are:

m.p. 136° C.; $^1$H n.m.r. (CDCl$_3$); δ 1.35, S (6H), 3,3-Me$_2$; 2.94, S, (3H), N-Me; 6.62–8.12, m, (8H), aromatic H; 7.73, S, (1H), 2'-H; 8.55, d, (1H), 6-H.

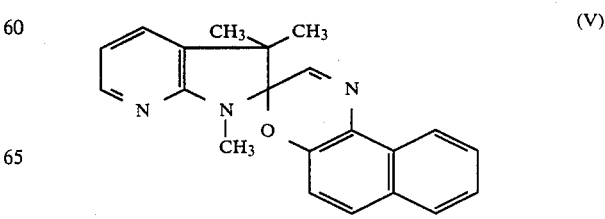

EXAMPLES 2 TO 7

Various other azaindoline spiro-oxazine compounds in accordance with the invention were synthesised by processes analogous to that described in Example 1. The compounds obtained together with their melting point, n.m.r. data and structural formulae are given below.

EXAMPLE 2

9'-Methoxy-1,3,3-trimethylspiro(7-azaindoline-2,3'-3H-naphtho(2,1-b)(1,4)oxazine) m.p. 189°–91° C., 'Hn.m.r. (CDCl$_3$); δ 1.36, S (6H), 3,3-Me$_2$; 2.99, S, (3H), N-Me; 4.00, S, (3H), O-Me; 6.60–8.60, m, (8H).

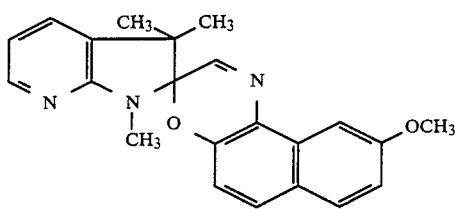

EXAMPLE 3

1,3,3-Trimethylspiro(7-azaindoline-2,3'-3H-pyrido(3,2-f)-(1,4)benzooxazine). m.p. 188° C., 'Hn.m.r. (CDCl$_3$); δ 1.37, S, (6H), 3,3-Me$_2$; 2.94, S, (3H) N-Me; 6.76–8.94, m, (8H), aromatic H; 7.76, S, (1H), 2'-H.

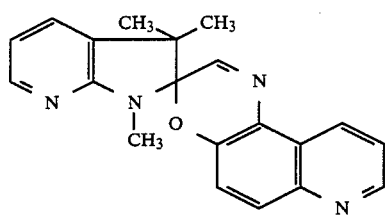

EXAMPLE 4

9'-Methoxy-1,3,3-trimethylspiro(4-azaindoline-2,3'-3H-naphtho(2,1,b)(1,4)oxazine). m.p. 151° C., 'Hn.m.r. (CDCl$_3$); δ 1.41, S, (6H), 3,3-Me$_2$; 2.78, S, (3H), N-Me; 4.00, S, (3H), O-Me; 6.69–7.90, m, (8H), aromatic H; 7.72, S, (1H), 2'-H.

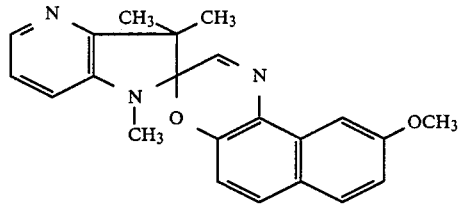

EXAMPLE 5

9'-Methoxy-1,3,3-trimethylspiro(4,7-diazaindoline)-2,3'-3H-naphtho(2,1-b)(1,4)oxazine). m.p. 131°–3° C., 'Hn.m.r. (CDCl$_3$); δ 1.41, S, (6H), 3,3,-Me$_2$; 2.97, S, (3H), N-Me; 4.01, S, (3H), O-Me; 6.78–7.88, m, (7H), aromatic H; 7.71, S (1H), 2'-H.

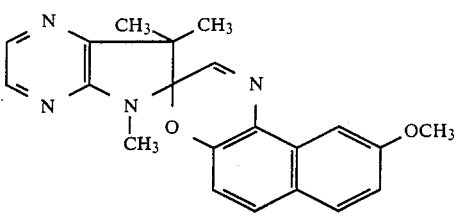

EXAMPLE 6

6-Methoxy-1,3,3,trimethylspiro(7-azaindoline-2,3'-3H-naphtho(2,1-b)(1,4)oxazine). m.p. 174°–5° C., 'H n.m.r. (CDCl$_3$); δ 1.31, S, (6H), 3,3-Me$_2$; 2.91, S, (3H), N-Me; 3.91, S, (3H), O-Me; 6.12, d, (1H), 4-H; 6.95–8.61, m, (7H), aromatic H; 7.72, S, (1H) 2'-H.

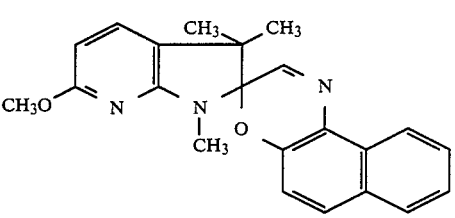

EXAMPLE 7

1,3,3,6-Tetramethylspiro(7-azaindoline-2,3'-3H-naphtho(2,1-b)(1,4)oxazine) m.p. 162°–3° C. 'Hn.m.r. (CDCl$_3$); δ 1.33, S, (6H), 3,3-Me$_2$; 2.47, S, (3H), 6-Me; 2.94, S, (3H), N-Me; 6.52–8.61, m, (8H), aromatic H; 7.73, S, (1H), 2'-H.

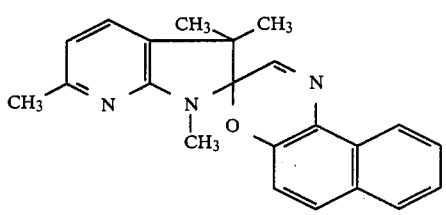

EXAMPLE 8

1,3,3,5-Tetramethylspiro(7-azaindoline-2,3'-3H-naphtho(2,1-b)(1,4)oxazine) m.p. 150° C. 'Hn.m.r. (CDCl$_3$); δ 1.33, S, (6H), 3,3-Me$_2$; 2.25, S, (3H), 5-Me; 2.90, S, (3H), N-Me; 6.92–8.62, m, (8H), aromatic H; 7.72, S, (1H), 2'-H.

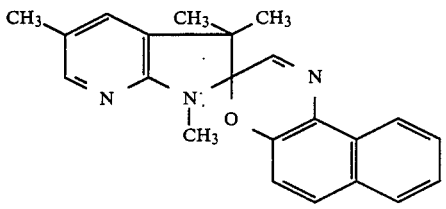

EXAMPLE 9

9'-Hydroxy-1,3,3-trimethylspiro(7-azaindoline-2,3'-3H-naphtho(2,1-b)(1,4)oxazine). m.p. 251° C., 'H n.m.r.

(CDCl$_3$); δ 1.35, S, (6H), 3,3-Me$_2$; 2.95, S, (3H), N-Me; 6.90–8.63, m, (8H), aromatic H; 7.68, S, (1H) 2'-H.

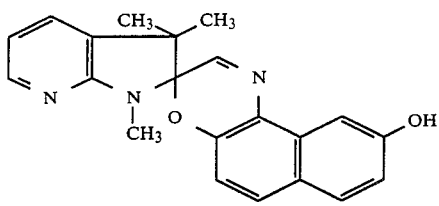

I claim:
1. An azaindoline spiro-oxazine compound having the general formula

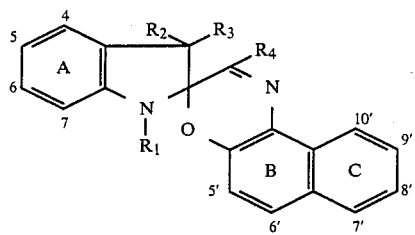

wherein R$_1$ represents a benzyl or C$_{1-4}$ alkyl group; each of R$_2$ and R$_3$ independently represents a phenyl, benzyl or C$_{1-4}$ alkyl group; R$_4$ represents a hydrogen atom, or an alkyl, aryl, or heteroaryl group; ring A contains one or more nitrogen atoms in the ring and is unsubstituted or substituted by a C$_{1-4}$ alkyl or C$_{1-4}$ alkoxy group, provided that there is no substituent on any nitrogen atom in the ring; ring B is unsubstituted; and ring C is a benzene nucleus or contains one or more nitrogen atoms in the ring and is unsubstituted or substituted by a hydroxyl or C$_{1-4}$ alkoxy group at position 9'.

2. A compound according to claim 1 in which ring A contains an unsubstituted nitrogen atom at the 4-position.

3. A compound according to claim 1 in which ring A contains an unsubstituted nitrogen atom at the 7-position.

4. A compound according to claim 1 in which the ring A contains unsubstituted nitrogen atoms at the 4-position and at the 7-position.

5. A compound according to claim 3 which is 1,3,3-Trimethylspiro(7-azaindoline-2-3'-3H-naphtho(2,1-b)(1,4)-oxazine).

6. A compound according to claim 3, which is 9'-Methoxyl-1,3,3-trimethylspiro(7-azaindoline-2,3'-3H-naphtho(2,1-b)(1,4)oxazine).

7. A compound according to claim 3, which is 1,3,3 Trimethylspiro(7-azaindoline-2,3'-3H-pyrido(3,2,-f)-(1,4)benzooxazine).

8. A compound according to claim 2, which is 9'-Methoxy-1,3,3-trimethylspiro(4-azaindoline-2,3'-3H-naphtho(2,1-b)(1,4)oxazine).

9. A compound according to claim 4, which is 9'-Methoxy-1,3,3-trimethylspiro(4,7-diazaindoline)-2,3'3H-naphtho(2,1-b)(1,4)oxazine).

10. A compound according to claim 3, which is 6-Methoxy-1,3,3-trimethylspiro(7-azaindoline-2,3'-3H-naphtho(2,1-b)(1,4)oxazine).

11. A compound according to claim 3, which is 1,3,3,6-Tetramethylspiro(7-azaindoline-2,3'-3H-naphtho(2,1-b)(1,4)oxazine).

12. A compound according to claim 3, which is 1,3,3,5-Tetramethylspiro(7-azaindoline-2,3'-3H-naphtho(2,1-b)(1,4)oxazine).

13. A compound according to claim 3, which is 9'-Hydroxy-1,3,3-trimethylspiro(7-azaindoline-2,3'-3H-naphtho(2,1-b)(1,4)oxazine.

* * * * *